(12) United States Patent
Creaturo

(10) Patent No.: US 9,775,950 B2
(45) Date of Patent: Oct. 3, 2017

(54) SYRINGE WITH DOSAGE INDICATOR FOR THE VISUALLY IMPAIRED

(71) Applicant: Parenteral Technologies, LLC, Siesta Key, FL (US)

(72) Inventor: Michael A. Creaturo, Siesta Key, FL (US)

(73) Assignee: Parenteral Technologies, LLC, Siesta Key, FL (US)

( * ) Notice: Subject to any disclaimer, the term of this patent is extended or adjusted under 35 U.S.C. 154(b) by 163 days.

(21) Appl. No.: 14/596,675

(22) Filed: Jan. 14, 2015

(65) Prior Publication Data

US 2015/0196714 A1    Jul. 16, 2015

Related U.S. Application Data

(60) Provisional application No. 61/927,157, filed on Jan. 14, 2014.

(51) Int. Cl.
*A61M 5/31* (2006.01)
*A61M 5/32* (2006.01)
*A61M 5/315* (2006.01)

(52) U.S. Cl.
CPC ...... *A61M 5/3129* (2013.01); *A61M 5/31526* (2013.01); *A61M 5/31533* (2013.01); *A61M 5/31595* (2013.01); *A61M 5/3243* (2013.01); A61M 2005/3125 (2013.01); A61M 2205/581 (2013.01); A61M 2205/582 (2013.01)

(58) Field of Classification Search
CPC ............ A61M 5/3129; A61M 5/31525; A61M 5/31526; A61M 5/31528; A61M 5/3153; A61M 5/31531; A61M 5/31533; A61M 5/31535; A61M 5/3156; A61M 5/315653; A61M 5/31568; A61M 5/3157; A61M 5/31573; A61M 5/31576; A61M 5/31578; A61M 5/3159; A61M 5/31591; A61M 5/31593; A61M 5/31595; A61M 2205/58; A61M 2205/581; A61M 2205/582
See application file for complete search history.

(56) References Cited

U.S. PATENT DOCUMENTS 5,009,645 A * 4/1991 Silver ............... A61M 5/31555
604/207
6,099,504 A * 8/2000 Gross ................. A61M 5/2046
604/140
7,081,107 B2 7/2006 Kito et al.
(Continued)

OTHER PUBLICATIONS

International Search Report and Written Opinion of the International Searching Authority of corresponding International Application No. PCT/US2015/011354; dated May 6, 2015; 6 pages.

*Primary Examiner* — Imani Hayman
*Assistant Examiner* — James D Ponton
(74) *Attorney, Agent, or Firm* — Shumaker, Loop & Kendrick, LLP

(57) ABSTRACT

A syringe including a barrel having an internal reservoir for containing a volume of medication, a plunger received within the barrel and axially movable relative thereto to change the volume of medication in the reservoir, and a dosage indicator movable with the plunger, the dosage indicator in contact with the barrel such that at least one of an audible alert and a tactile alert is produced upon movement of the dosage indicator relative to the barrel.

16 Claims, 23 Drawing Sheets

(56) References Cited

U.S. PATENT DOCUMENTS

| | | |
|---|---|---|
| 7,575,570 B2 | 8/2009 | Barere |
| 2002/0088131 A1* | 7/2002 | Baxa ................. A61M 5/31525 33/494 |
| 2006/0184136 A1 | 8/2006 | Kleyman et al. |
| 2011/0118701 A1* | 5/2011 | Baney ............... A61M 5/31595 604/506 |
| 2011/0313397 A1* | 12/2011 | Gold ................. A61M 5/31551 604/506 |
| 2013/0079718 A1 | 3/2013 | Shang et al. |
| 2013/0090603 A1* | 4/2013 | Hoyle, Jr. ........... A61M 5/3129 604/189 |
| 2013/0197449 A1* | 8/2013 | Franklin ........... A61M 5/31526 604/209 |
| 2013/0303985 A1 | 11/2013 | Wotton et al. |

* cited by examiner

SYRINGE WITH DOSAGE INDICATOR FOR THE VISUALLY IMPAIRED

CROSS-REFERENCE TO RELATED APPLICATION

This application claims priority from U.S. application No. 61/927,157 filed Jan. 14, 2014, the entirety of which is incorporated by reference herein.

TECHNICAL FIELD AND BACKGROUND OF THE INVENTION

The present invention relates generally to enhancing the safety and self-administration of injectable medication for the visually impaired, and more particularly, to syringes and other injection devices including one or more of a tactile and audible indicator for ensuring dosage accuracy.

According to the American Diabetes Association, data from 2011 shows the prevalence of Diabetes in the U.S. at 8.3% of the population, affecting approximately 25.8 million children and adults. The total cost of diagnosed diabetes in 2012 was estimated to be 245 billion, with 176 billion attributable to direct costs and 69 billion attributable to reduced productivity. Diabetes is not only a growing concern in the U.S., but an emerging threat worldwide. The World Health Organization estimates that 347 million people worldwide suffer from diabetes. In 2004, it was estimated that 3.4 million people died from diabetes-related illness. The World Health Organization predicts that diabetes will become the seventh leading cause of death by the year 2030.

A common complication associated with diabetes is vision impairment. According to the American Diabetes Association, diabetes is the leading cause of new cases of blindness among adults age 20-74. From 2005-2008, it was estimated that 4.2 million diabetics over the age of 40 suffered some degree of diabetic retinopathy, and of these, almost 700 thousand suffered from advanced diabetic retinopathy leading to severe vision loss.

Vision impairment and loss are of particular concern for insulin-dependent diabetics that require daily injections. The loss or worsening of vision presents a significant challenge in self-administering injections, particularly in terms of dosage accuracy. While devices have been developed to aid the visually impaired in self-administering injections, these conventional devices are either prohibitively expensive or difficult to use. Accordingly, the majority of insulin-dependent diabetics rely on others to administer their daily injections.

BRIEF SUMMARY OF THE INVENTION

Therefore, it is an object of the invention to provide a safety syringe for aiding the visually impaired in self-administering injectable medications.

It is another object of the invention to provide a syringe that is cost-effective and easy to use.

It is yet another object of the invention to provide a syringe that has a dosage indicator for determining with a great degree of accuracy the quantity of medication loaded into and delivered from the syringe.

It is yet another object of the invention to provide a syringe including one or more of a tactile and an audible dosage indicator.

It is yet another object of the invention to provide a syringe that provides the user with one or more of a tactile and an audible report as the plunger is moved relative to the barrel.

It is yet another object of the invention to provide a kit for aiding the blind in self-administering injections, the kit including one or more of a safety syringe with a tactile and/or audible dosage indicator for the visually impaired, a medication container holding a volume of medication, and packaging with indicia indicating to the visually impaired the contents of the kit and other pertinent data.

To achieve the foregoing and other objects and advantages, provided herein is a syringe including a barrel having an internal reservoir for containing a volume of medication, a plunger received within the barrel and axially movable relative thereto to change the volume of the medication in the internal reservoir, and a dosage indicator movable with the plunger, the dosage indicator in contact with the barrel such that at least one of an audible alert and a tactile alert is produced upon movement of the dosage indicator relative to the barrel.

In a further embodiment, the dosage indicator may include a collar positioned around the barrel configured to slide along a length of the barrel as the plunger moves axially, an interior of the collar contacting external features on the barrel to produce the at least one of an audible alert and a tactile alert to indicate collar movement.

In a further embodiment, the collar may be attached to a plunger flange of the plunger through a pair of parallel spaced arms.

In a further embodiment, the parallel spaced arms may travel along diametrically opposing flat faces of the barrel.

In a further embodiment, the parallel spaced arms may travel within elongate slots recessed into an outer surface of the barrel.

In a further embodiment, the collar may include an internal feature arranged to contact the external features on the barrel to provide stepped motion of the collar along the length of the barrel.

In a further embodiment, the collar may include a window aligned with a face of the barrel such that dosage indicia marked on the barrel is displayed through the window.

In a further embodiment, the collar may include a pair of diametrically opposing windows aligned with respective diametrically opposing flat faces of the barrel, and wherein raised dosage indicia marked on the opposing flat faces of the barrel is displayed through the windows.

In a further embodiment, the barrel may be marked with raised indicia including at least one of braille, numbers, major graduations and minor graduations.

In a further embodiment, the syringe may include a needle guard configured to retract into the barrel to expose a needle attached to one end of the barrel.

In a further embodiment, the needle guard may be biased in a direction away from the plunger.

In a further embodiment, the syringe may include a lock arranged on a barrel flange of the barrel movable into and out of contact with the plunger, the lock movable between a first position preventing relative axial movement between the barrel and the plunger and a second position allowing relative axial movement between the barrel and the plunger.

In a further embodiment, the barrel may include diametrically opposing flat faces, wherein one flat face is marked with raised indicia including braille and major graduations and the opposing flat face is marked with raised indicia including major and minor graduations.

In a further embodiment, the plunger may include external features that contact internal features on a collar positioned atop a barrel flange of the barrel.

According to another embodiment, a syringe is provided herein configured to produce at least one of an audible and a tactile alert to a visually impaired user to indicate dosage of a medication, the syringe including a barrel having an internal reservoir for containing a volume of the medication, a plunger received within the barrel and axially movable relative thereto to change the volume of the medication in the internal reservoir, and a dosage indicator movable with the plunger, the dosage indicator including collar positioned around the barrel configured to produce at least one of an audible and a tactile alert in response to relative movement between the plunger and the barrel.

In a further embodiment, the collar may be connected to the plunger through a pair of parallel spaced arms, and wherein an interior of the collar contacts external features on the barrel to produce the at least one of an audible and tactile alert in response to plunger movement.

In a further embodiment, the collar may include a window aligned with a flat face of the barrel such that raised dosage indicia marked on the barrel is presented through the window.

In a further embodiment, the collar may include a pair of diametrically opposing windows aligned with respective diametrically opposing flat faces of the barrel, and wherein raised dosage indicia marked on the opposing flat faces of the barrel is presented through the windows.

In a further embodiment, the barrel may be marked with raised indicia including at least one of braille, numbers, major graduations and minor graduations.

In a further embodiment, the syringe may include a needle guard configured to retract into the barrel to expose a needle attached to one end of the barrel, wherein the needle guard is biased in a direction away from the plunger.

Embodiments of the invention can include one or more or any combination of the above features, aspects and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as claimed. The accompanying drawings are included to provide a further understanding of the invention, and are incorporated in and constitute a part of this specification.

BRIEF DESCRIPTION OF THE DRAWINGS

Features, aspects and advantages of the present invention are better understood when the following detailed description of the invention is read with reference to the accompanying drawings, in which.

DETAILED DESCRIPTION OF THE INVENTION

Figure 1:
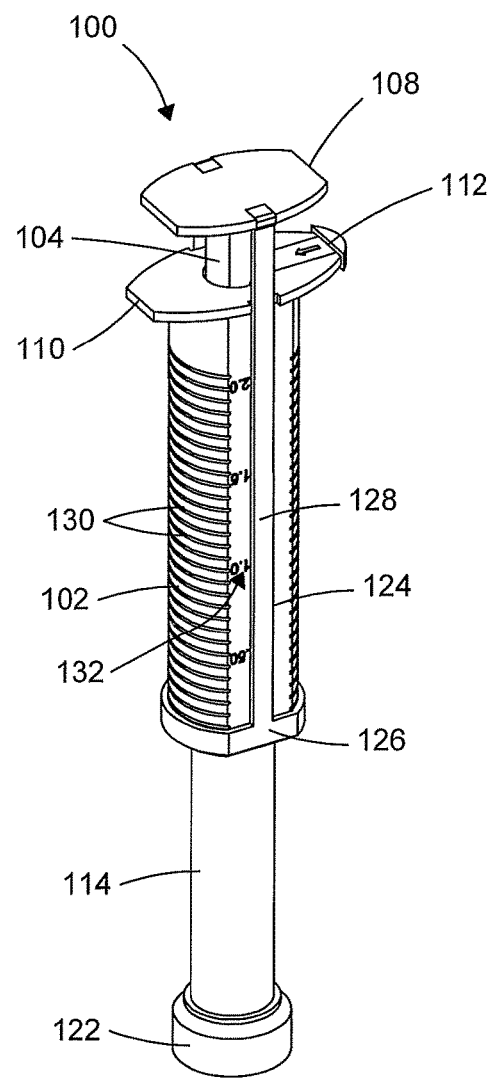
FIG. 1 is an isometric view of a syringe according to a first embodiment of the invention.

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

Referring to FIGS. 1-9, a first embodiment of a syringe including a dosage indicator for aiding the visually impaired is shown generally at reference numeral 100. Syringe 100 generally includes a barrel 102 having an internal reservoir for holding a volume of medication in liquid form, and a plunger 104 axially movable relative to the barrel to change the volume of medication in the barrel. A needle 106 attaches to one end of the barrel 102, and the opposing end of the barrel is open to receive one end of the plunger 104 therein. The barrel 102 shown is generally cylindrical with at least one flat face for displaying indicia, however, other shapes are envisioned. A seal is provided between one end of the plunger 104 and the inner wall of the barrel 102 such that the medication in the reservoir is not able to pass beyond the plunger. As such, the medication is forced through the needle as the plunger 104 is axially advanced into the barrel 102.

The plunger 104 terminates at the opposing end from the seal in a laterally extending plunger flange 108. The barrel 102 includes a corresponding barrel flange 110 that also extends laterally outward. In use, the flanges 108, 110 are gripped and pulled axially apart to withdraw the plunger 104 from the barrel 102 to "load" the syringe 100, and are gripped and compressed toward each other in the axial direction to force the medication through the needle 106. The barrel 102 and plunger 104 may be keyed, for example by way of a key and keyway, to prevent rotation therebetween. While preventing rotational movement may not be critical in conventional syringes devoid of a dosage indicator, preventing rotational movement between the plunger may be necessary in the embodiments provided herein, as described in further detail below. In each of the syringe embodiments described herein, the barrel 102 and plunger 104 have corresponding generally cylindrical cross-sections with diametrically opposing flat sides to locate raised indicia (e.g., Braille) to enhance tactile identification, and prevent rotation therebetween when engaged.

Figure 2:
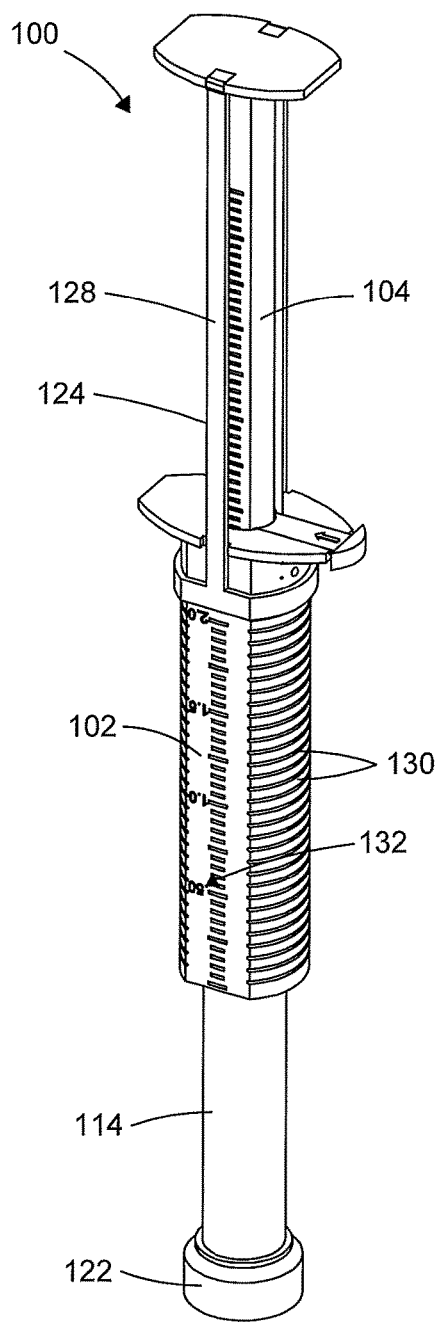
FIG. 2 shows the plunger withdrawn from the barrel and the needle guard in an operative position.
Figure 3:
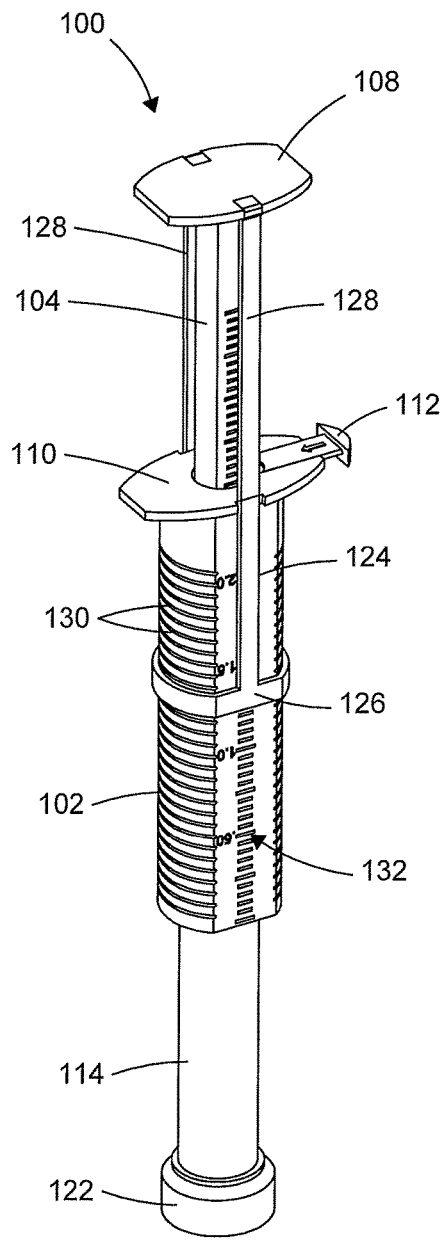
FIG. 3 shows a plunger lock in a non-operative position.
Figure 4:
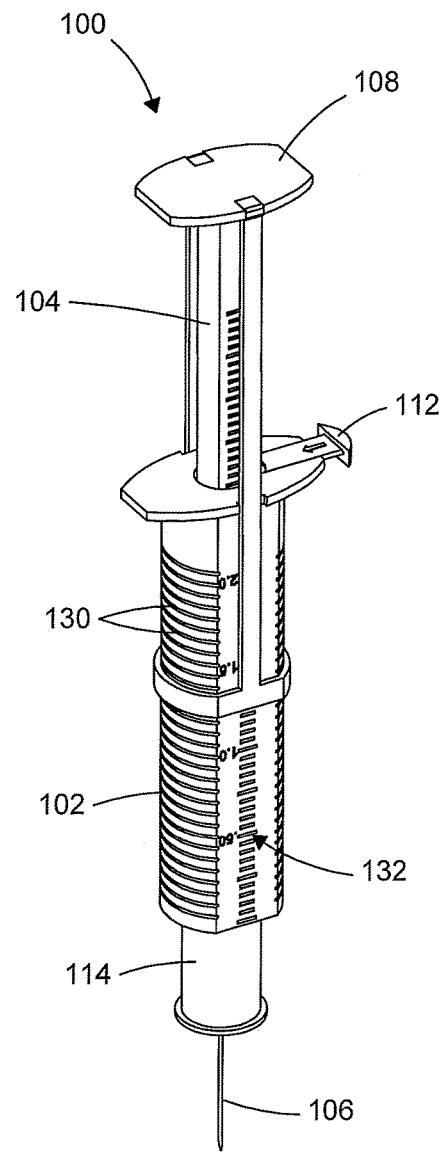
FIG. 4 shows the plunger lock in an operative position and the needle guard retracted.

Syringe 100 includes a lock 112 for locking axial movement of the plunger 104 relative to the barrel 102. The lock 112 may be incorporated into the barrel flange 110. The lock 112 functions to prevent the plunger 104 from moving axially relative to the barrel 102 by engaging with a detent, projection, recess or other structure located on the plunger, or alternatively, by way of interference with the plunger. As shown in FIG. 2, the lock 112 is shown in the operative or "locked" position engaging the plunger 104, thereby preventing relative axial movement between the plunger and barrel. As shown in FIG. 3, the lock 112 is shown in the non-operative or "unlocked" position out of engagement with the plunger 104, thereby allowing relative axial movement between the plunger and barrel. The lock 112 is actuated by sliding it in the lateral direction into and out of engagement with the plunger 104, for example, by manipulating it with the thumb. The lock 112 may be engaged, for example, when the syringe is loaded with a predetermined dosage to prevent the medication from being prematurely discharged.

Figure 5:
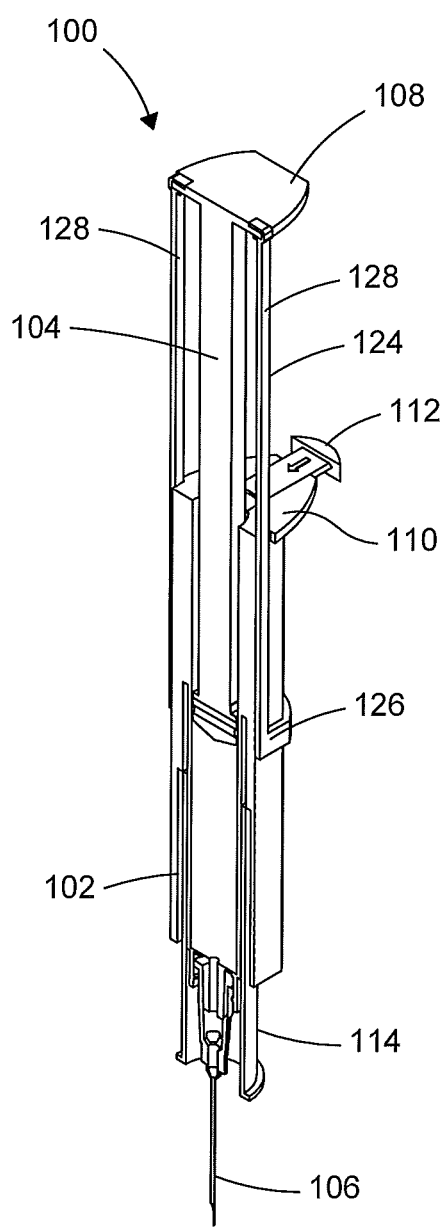
FIG. 5 is a sectional view through the syringe of FIG. 4.
Figure 6:
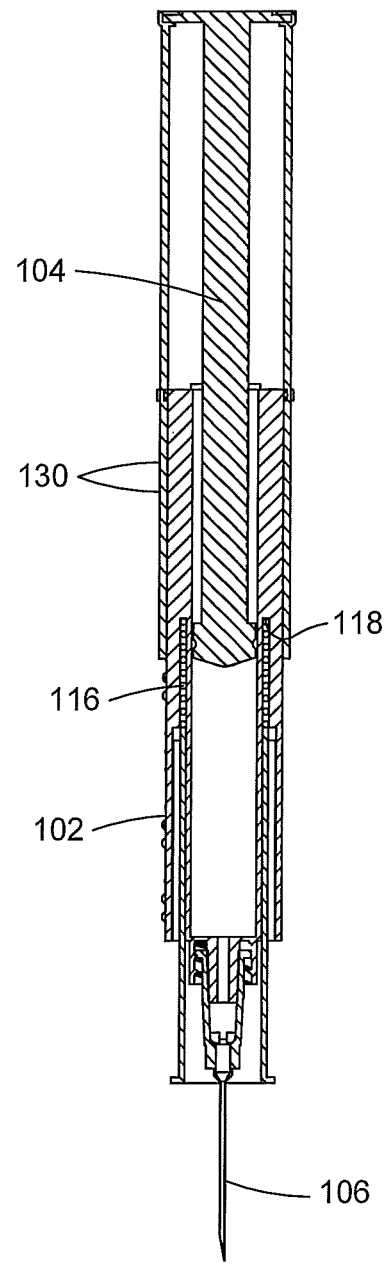
FIG. 6 is a longitudinal cross-sectional view through the syringe of FIG. 4.

The syringe 100 may further include a retractable needle guard 114 for preventing unintentional needle sticks. The needle guard 114 is shown fully extended in FIG. 2, and partially retracted into the barrel 102 in FIG. 4. When extended, the needle is concealed within the needle guard. When retracted or partially retracted, at least a portion of the needle is exposed and presented for insertion. The needle guard 114 may retract into an annular spaced defined in the barrel 102 as shown in FIGS. 5 and 6. The needle guard 114 may be spring biased or the like in the direction of the needle tip such that the needle guard retracts into the barrel 102 as the needle is advanced into the user's body, and automatically returns to the operative position concealing the needle when the needle is withdrawn from the user's body. Needle guard biasing may be achieved by way of a spring 116 positioned between the needle guard 114 and a shoulder 118 defined in the barrel. When compressed, the spring 116 urges against the shoulder 118 and the end of the needle guard 114, urging the needle guard in the direction of the needle tip. The needle guard 114 may have an annular bead 120 at one end thereof that engages an annular stop, for example an annular ring, on the inside of the barrel 102 to prevent the needle guard 114 from being pulled apart from the barrel 102. The syringe 100 may further include a removable safety cap 122.

Syringe 100 further includes a dosage indicator 124 for facilitating dosage accuracy for the visually impaired. The dosage indicator 124 may be an extension of the plunger 104, and may engage along the outer surface of the barrel 102 as the plunger 104 is axially advanced into and withdrawn from the barrel. The dosage indicator may be a separate component adapted to attach to the plunger or may be integrally formed with the plunger 104.

The dosage indicator 124 includes a collar 126 or "band" that circumferentially surrounds and engages a portion of the exterior surface of the barrel 102. A pair of elongate, diametrically opposed legs 128 interconnect the collar 126 and plunger flange 108, thereby locking movement of the collar and plunger flange together and preventing rotation therebetween. The collar 126 is shaped to closely conform to the contour of the underlying outer barrel circumference such that a relatively tight fit is provided therebetween. The spaced legs 128 stably support the collar 126 perpendicular to the longitudinal axis of the barrel 102. As shown, the legs 128 are arranged to slide along the length of the flat faces of the barrel 102, thereby preventing the dosage indicator 124 from twisting along the length of the barrel. Leg movement may further be guided with the aid of notches formed in the barrel flange 110.

Figure 7:
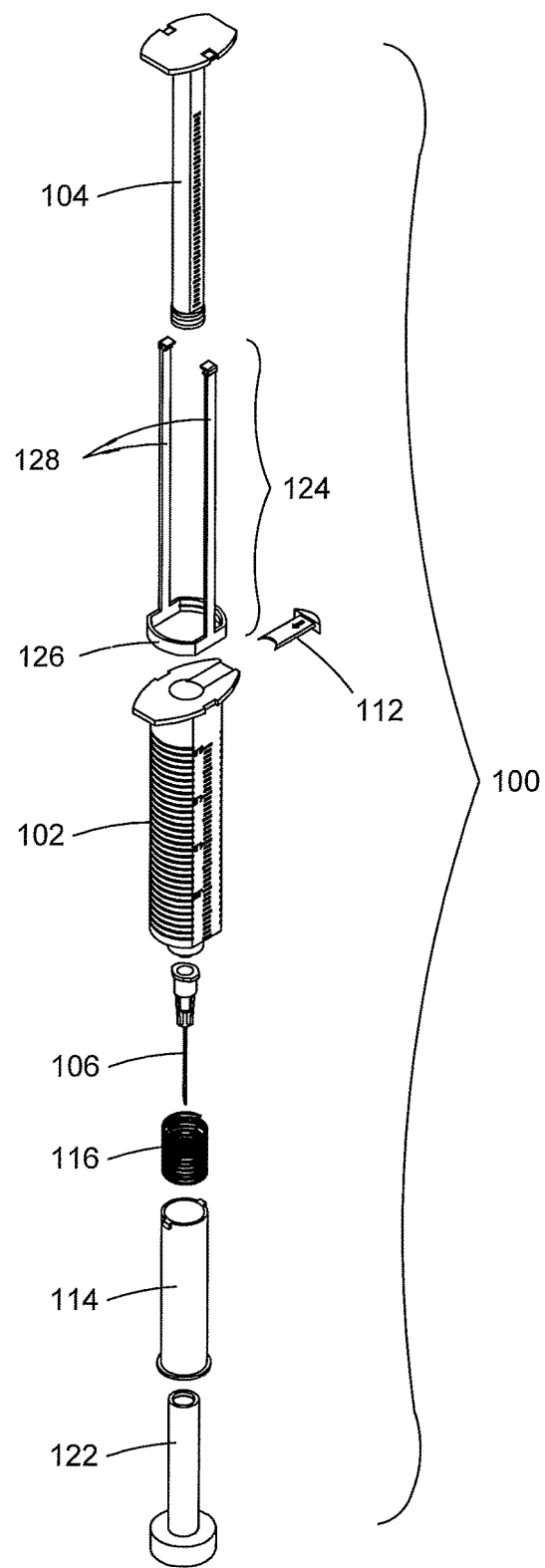
FIG. 7 is an exploded view of the syringe of FIG. 1.
Figure 8:
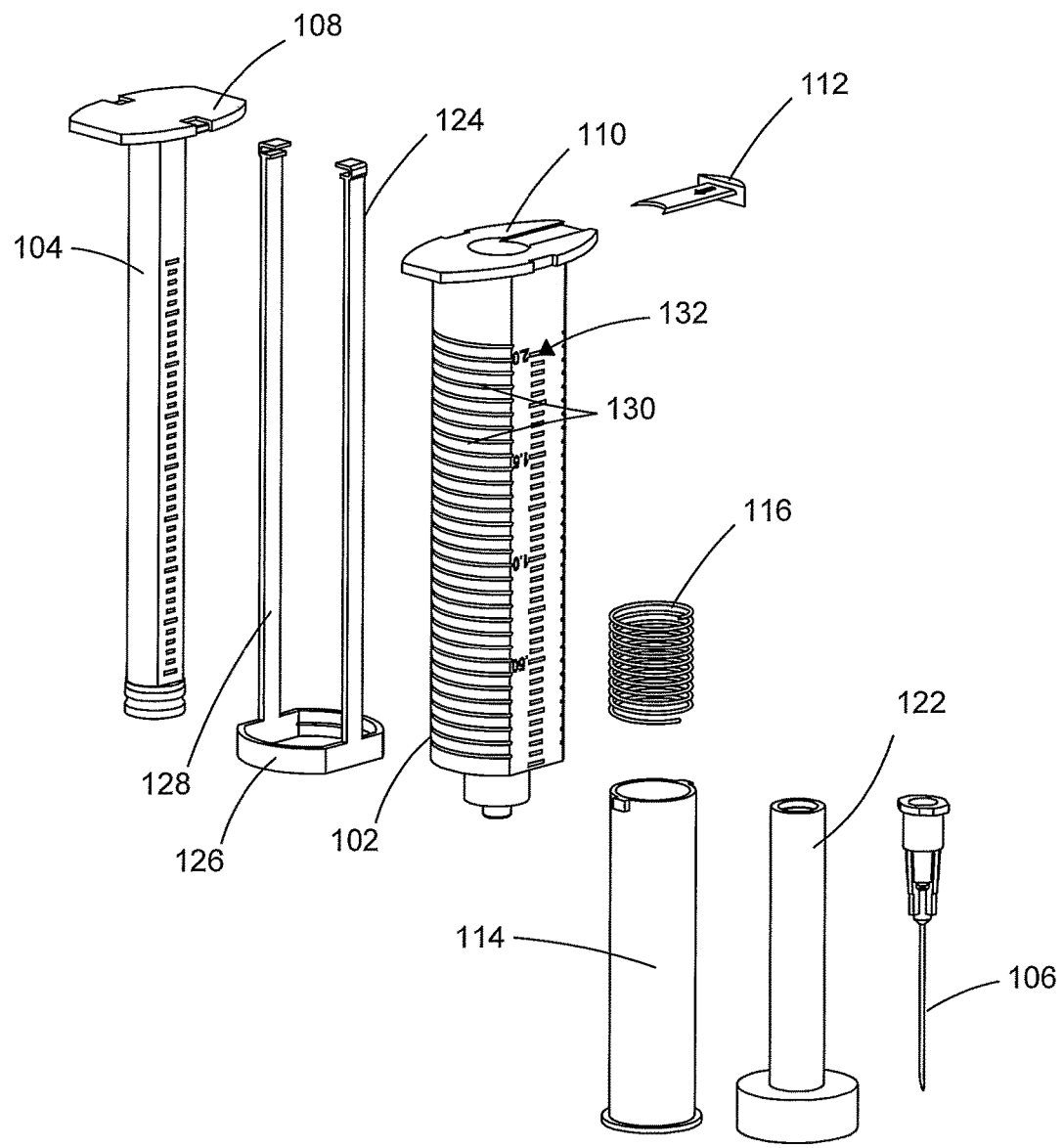
FIG. 8 shows the parts of the syringe of FIG. 1.
Figure 9:
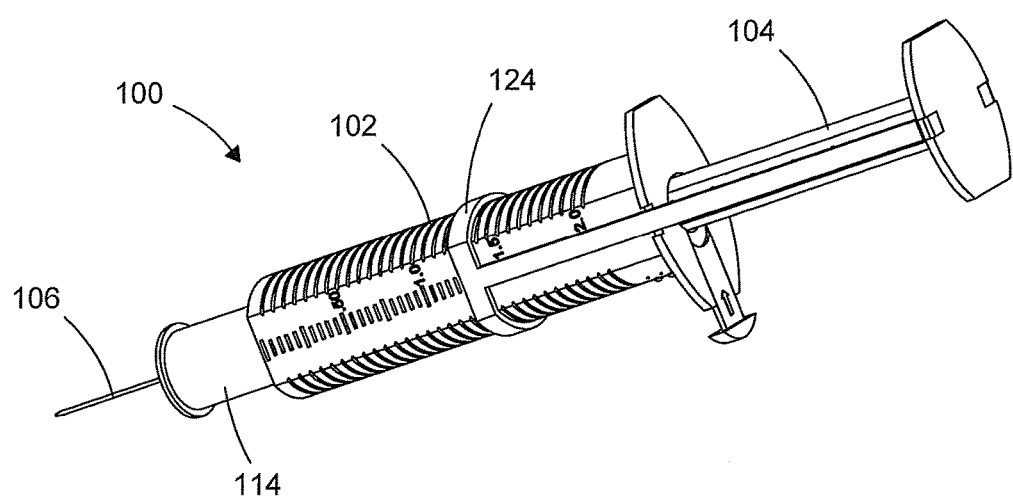
FIG. 9 is a perspective view of the syringe of FIG. 1.
Figure 10:
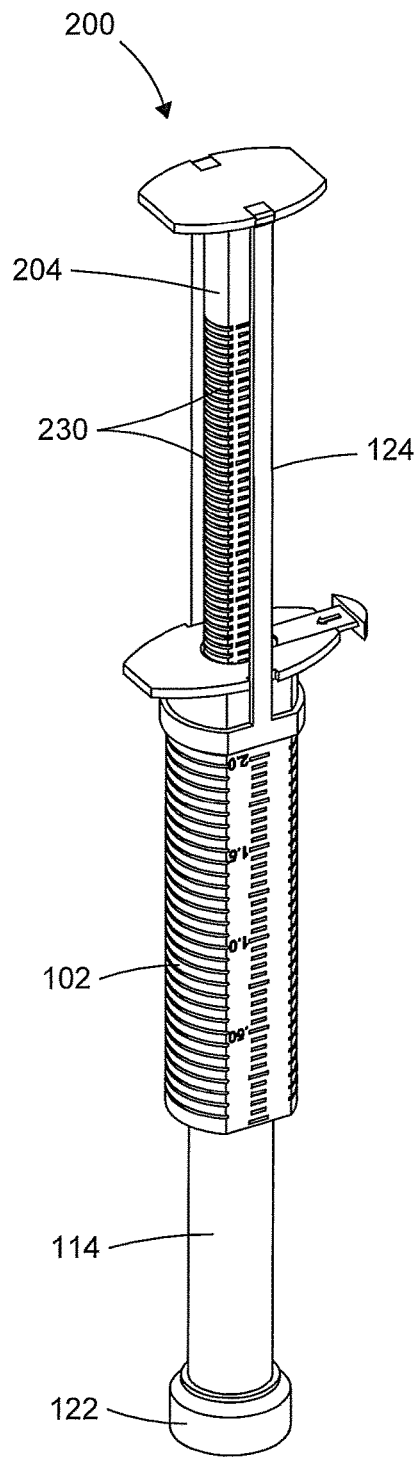
FIG. 10 is an isometric view of a syringe according to a second embodiment of the invention.
Figure 11:
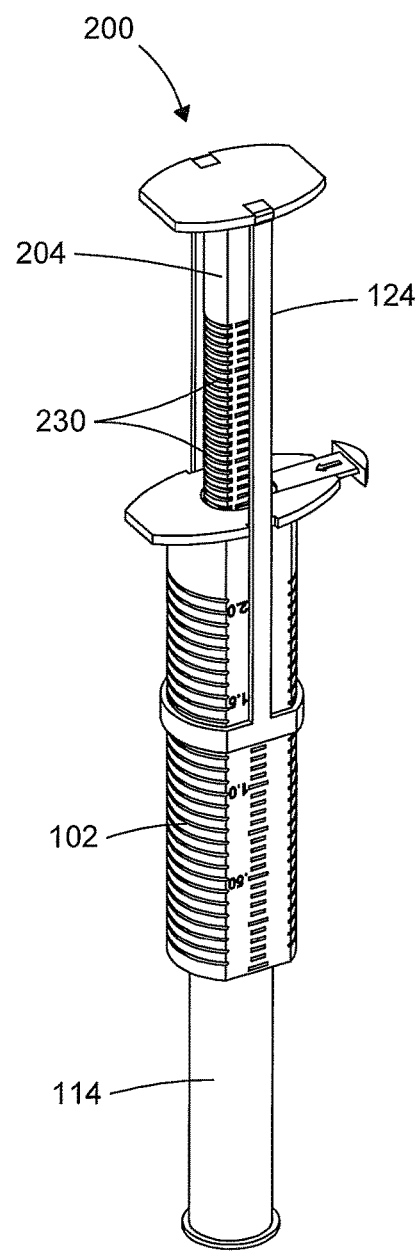
FIG. 11 shows the plunger partially advanced into the barrel.
Figure 12:
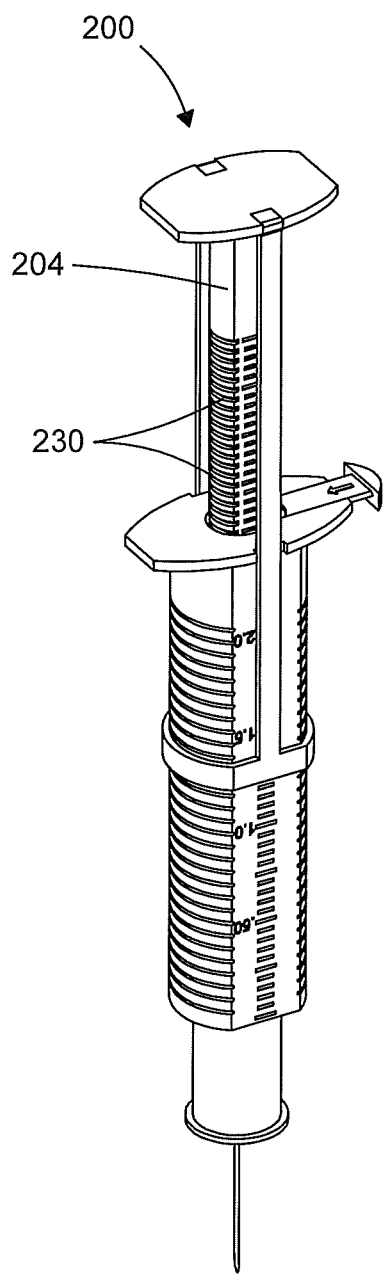
FIG. 12 shows the plunger lock in a non-operative position and the needle guard retracted into the barrel.

The outer surface of the barrel 102 is provided with a plurality of features 130 that contact the inner surface of the collar 126 to provide stepped movement of the collar along the length of the barrel. The term "features" as used herein generally refers to any detent, protrusion, projection, recess, ribbing, etc. positioned along the outer surface of the barrel 102. The features 130 are provided at regular intervals along the length of the barrel 102 and may correspond to any predetermined dosage measurement. The features 130 may be longitudinally spaced along the length of the barrel 102 and may correspond to graduations indicating volumetric measurement and/or other measurement. The features 130 may optionally include "large" or more pronounced features for certain predetermined increments (e.g., major graduations), and "small" or less pronounced features to indicate portions of the larger increments (e.g., minor graduations). As best shown in FIG. 7, corresponding or complementary features are provided on the inner surface of the collar positioned to contact the features 130 on the barrel 102 as the dosage indicator 124 slides along the length of the barrel.

The movement of the dosage indicator 124 relative to the barrel 102 may be stepped (i.e., not continuous), meaning that the collar 126 engages each feature 130 as it passes by to indicate to the user a tactile and/or audible report or "alert." In a specific embodiment, interference between the external features of the barrel and internal features of the collar results in a slight resistance or hesitation to axial movement, requiring additional force to move the collar passed each feature to prevent unintentional or unnoticed movement of the plunger. In this arrangement, the user is able to determine with great confidence the volume of medication loaded into and expelled from the barrel reservoir by way of the number of "clicks" or tactile alerts such as vibration from the dosage indicator movement.

The barrel 102 may further include raised indicia 132, for example Braille, indicating the volumetric measurements. The raised indicia and graduations may correspond to common dosages, for example, dosages common for insulin injections. Volumetric indicia may be provided on the barrel 102, for example, in terms of mL, IU, CC, MG, MCG, etc. Indicia may also be provided in terms of KG, LB, BSA (Body Surface Area), BMI (Body Mass Index), etc. Raised indicia may also be provided on the plunger.

Syringe 100 lacks a dosage window for indicating the dosage through the collar 126, therefore, the dosage may be determined by reading the dosage indicated along the leading or forward most edge of the collar. The dosage can be determined and confirmed by reading the dosage at the leading edge of the collar and/or counting the number of audible clicks or sensations felt while loading and/or administering the medication.

Figure 13:
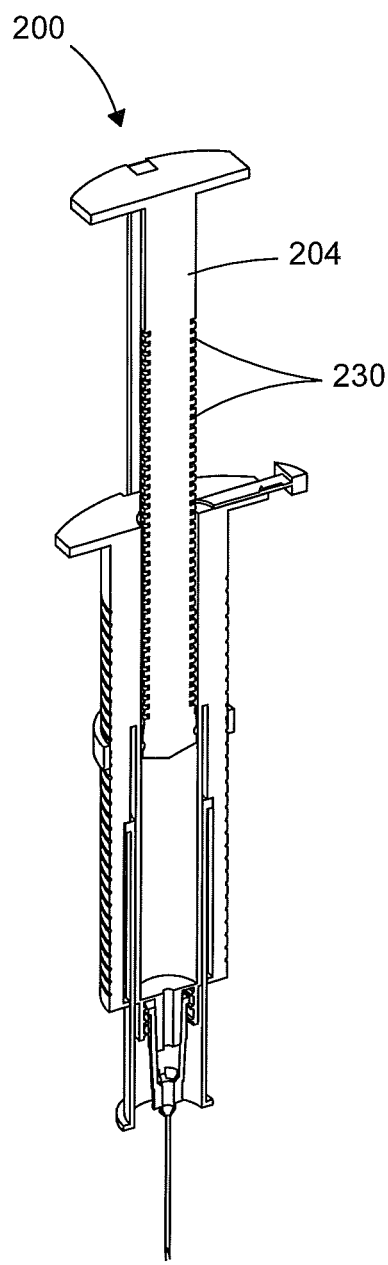
FIG. 13 is a sectional view through the syringe of FIG. 12.
Figure 14:
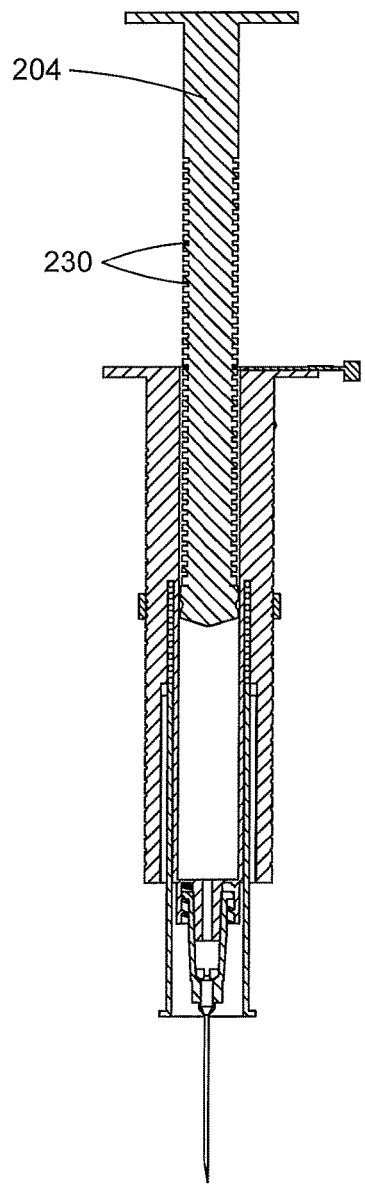
FIG. 14 is a longitudinal sectional view through the syringe of FIG. 12.
Figure 15:
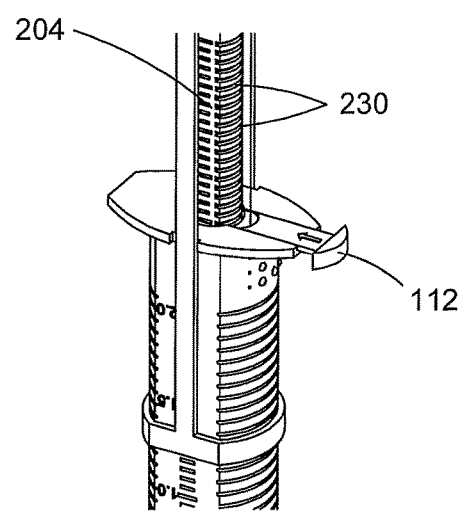
FIG. 15 is a detailed view of the plunger lock.
Figure 16:
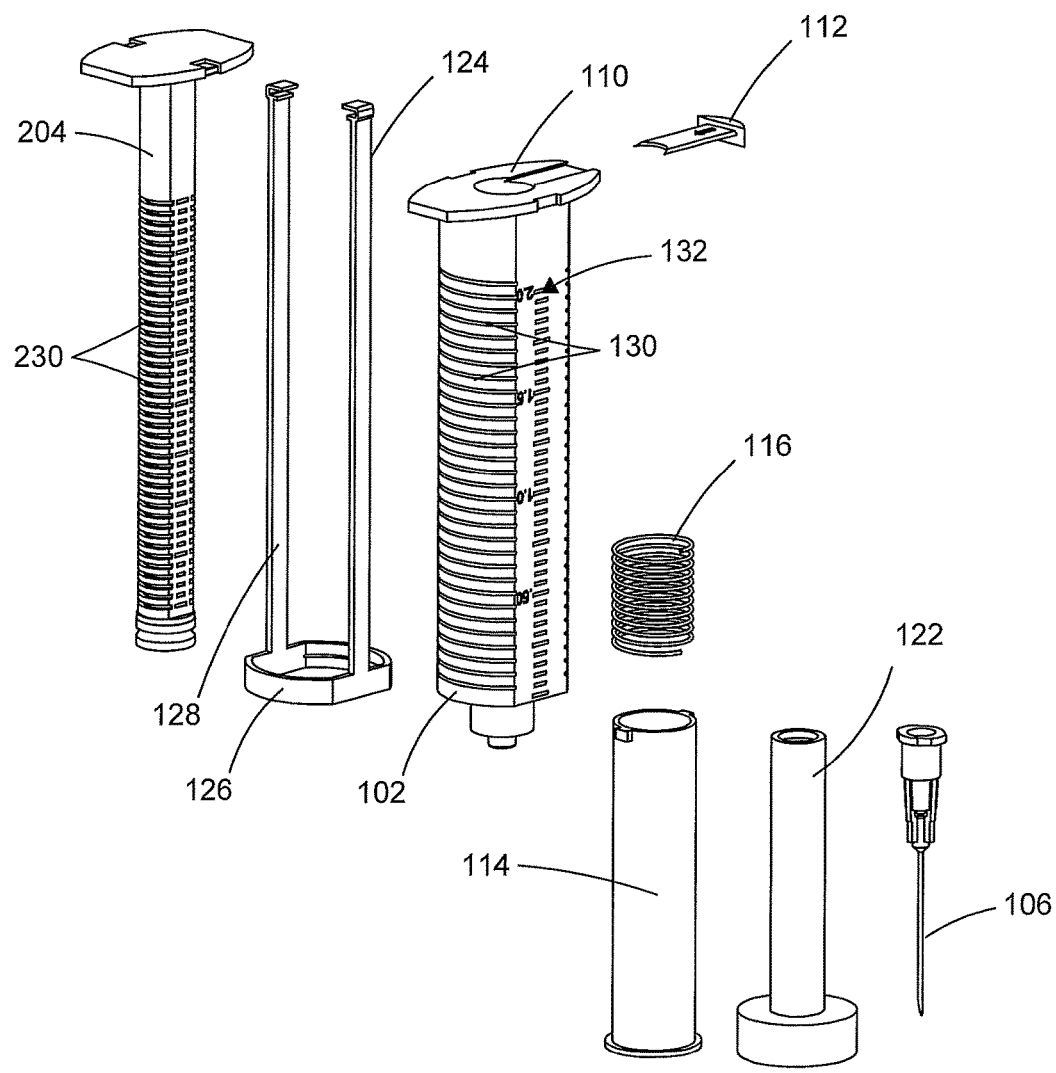
FIG. 16 shows the parts of the syringe of FIG. 10.

Referring to FIGS. 10-16, a second embodiment of a syringe including a dosage indicator for aiding the visually impaired is shown generally at reference numeral 200. Syringe 200 is similar to syringe 100 and therefore includes most of the same parts indicated at like reference numerals. The primary difference in syringe 200 is that the plunger 204 includes external features 230 similar to the external barrel features of syringe 100. In this configuration, features 230 may also, or in the alternative, report one or more of a tactile and audible alert to the user indicating plunger movement. As best shown in FIGS. 13 and 14, the plunger features 230 further provide detents positioned to engage/receive the lock 112 to lock the plunger to prevent axial movement between the plunger and barrel.

Figure 17:
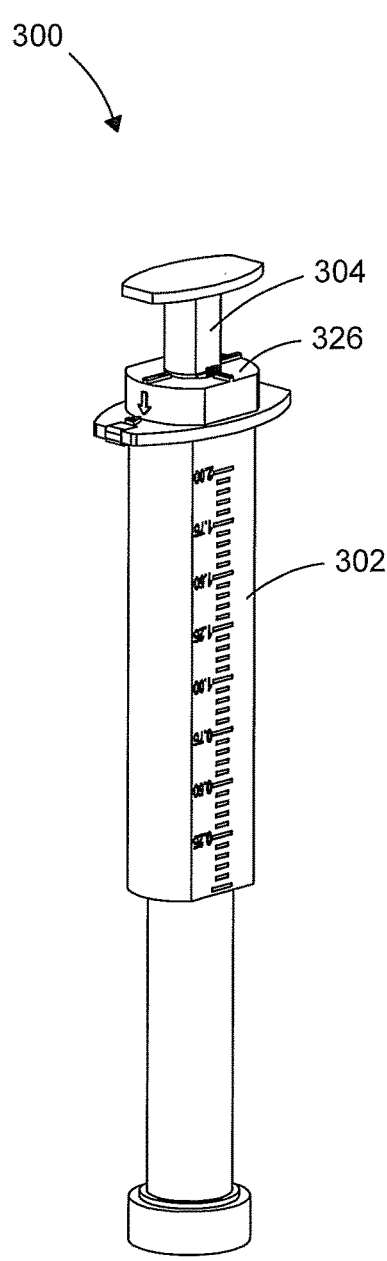
FIG. 17 is an isometric view of a syringe according to a third embodiment of the invention.
Figure 18:
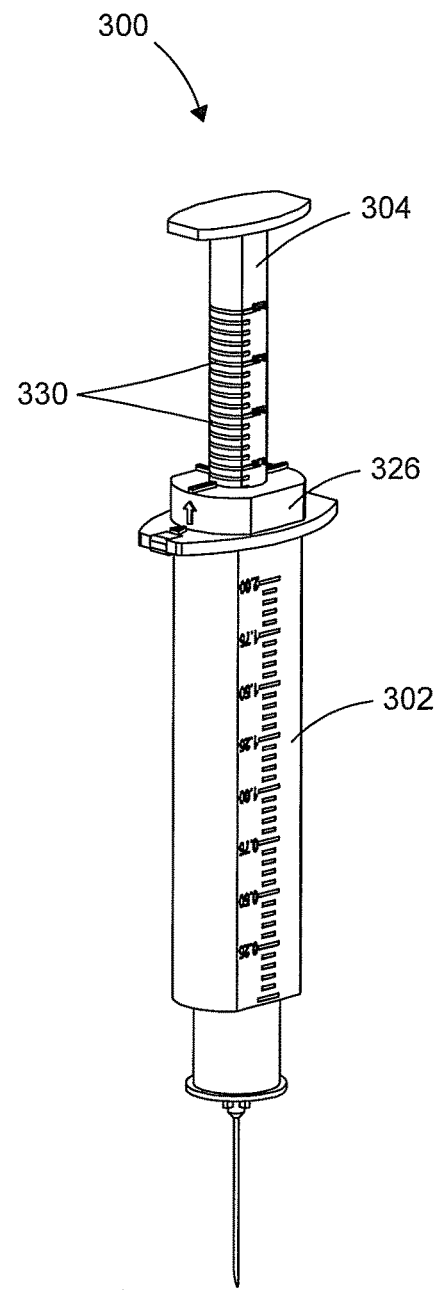
FIG. 18 shows the plunger partially withdrawn from the barrel and the needle guard retracted.
Figure 19:
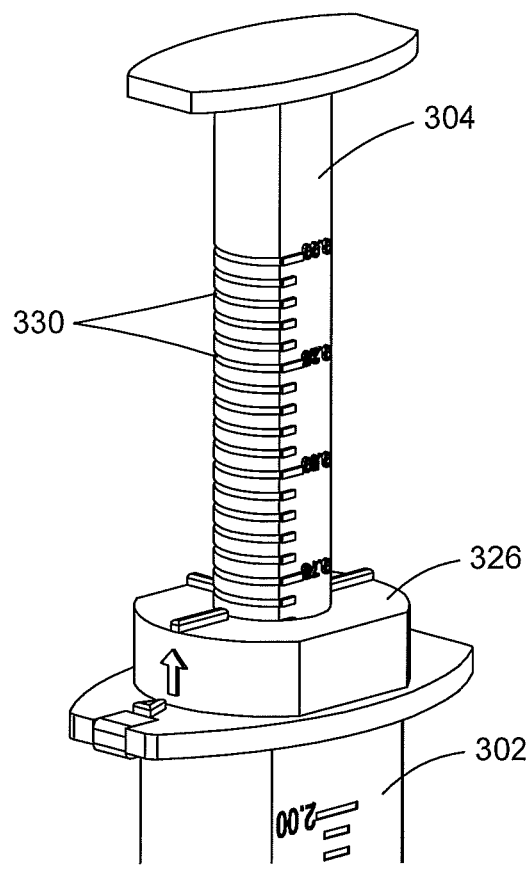
FIG. 19 is a detailed view of a collar positioned at an end of the barrel.

Referring to FIGS. 17-19, a third embodiment of a safety syringe including a dosage indicator for aiding the visually impaired is shown generally at reference numeral 300. Syringe 300 lacks the external dosage indicator of syringes 100 and 200 discussed above. Syringe 300 includes a barrel 302 lacking external detents, but retains indicia such as raised indicia for indicating the dosage. A collar 326 is positioned at the end of the barrel 302 atop the barrel flange. The collar 326 includes internal features that contact external features 330 positioned along the length of the plunger 304. In use, axial movement of the plunger 304 relative to the barrel 302 produces at least one of an audible and tactile alert to the user of plunger movement. The plunger 304 may be locked relative to the barrel 302 by actuating a thumb lock, or in the alternative, rotating or otherwise moving the collar relative to the barrel 302.

Figure 20:
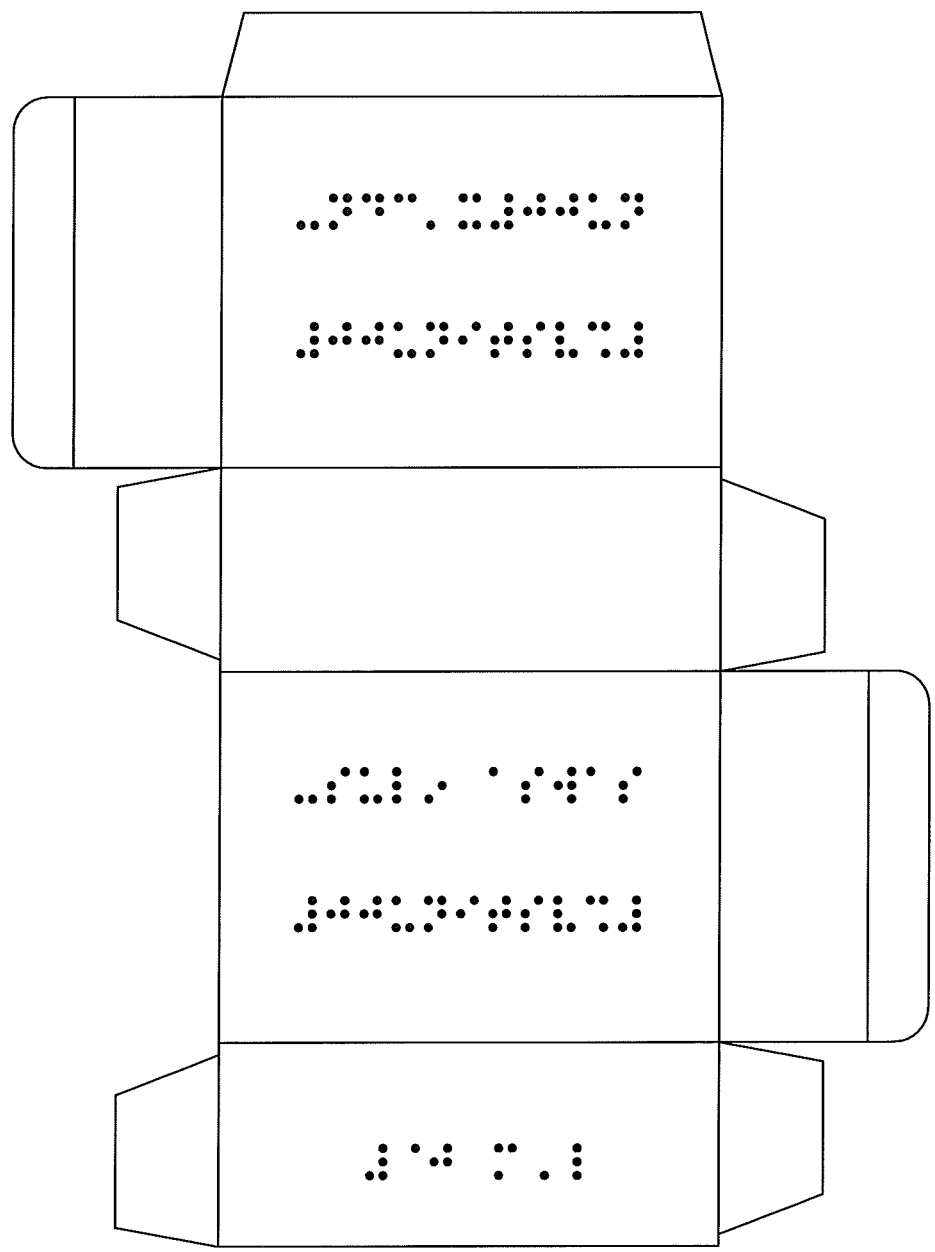
FIG. 20 shows an embodiment of syringe and/or medication packaging in an unfolded configuration and marked with Braille.
Figure 21:
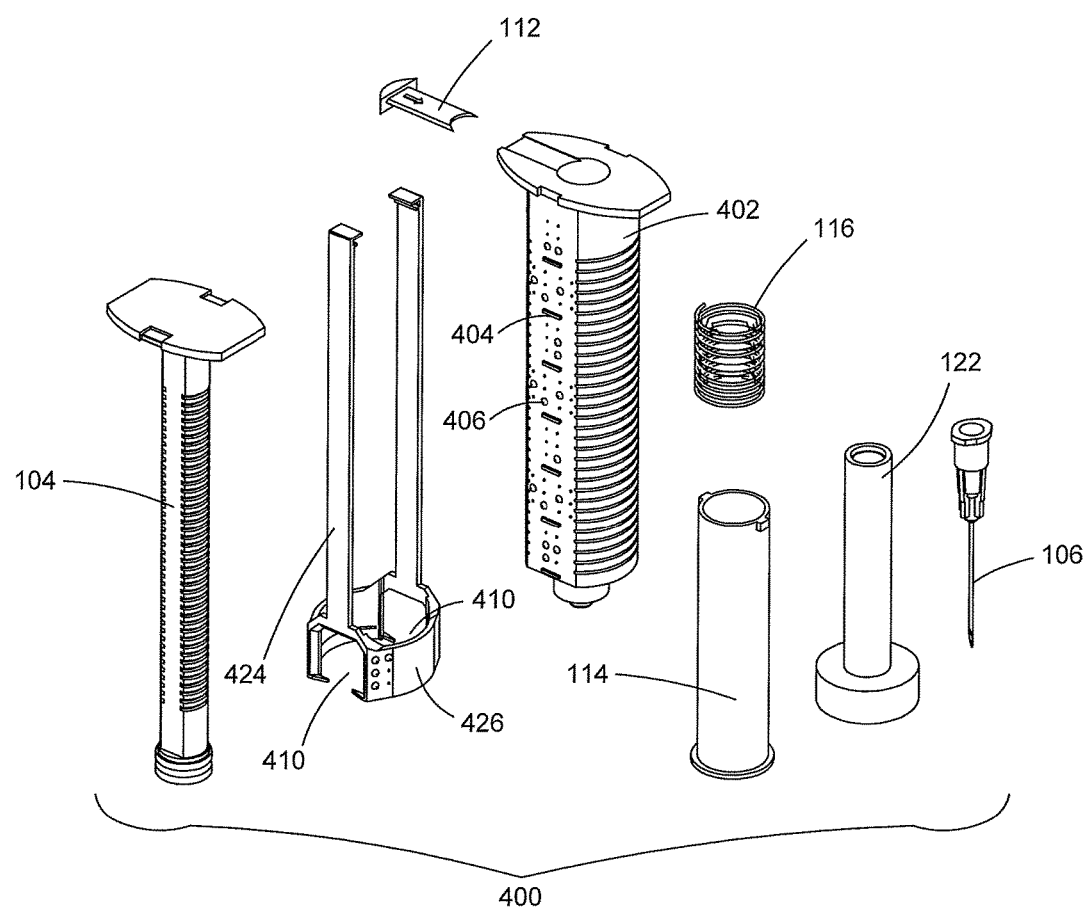
FIG. 21 is an exploded view of a syringe marked with Braille indicia according to a fourth embodiment of the invention.

While the syringe in any one of the foregoing and following embodiments may be marked with Braille to indicate to the visually impaired user at least one of dosage, medication type, date, etc., packaging accompanying the syringe and/or medication may be similarly externally marked with Braille to indicate the same. For example, a package containing a predetermined medication and/or syringe may be marked with Braille to indicate the contents of the packaging to the visually impaired user to ensure that the proper medication is used with the proper syringe calibrated for use with that predetermined medication. Exemplary Braille-marked packaging is shown in an unfolded configuration in FIG. 20.

Figure 22:
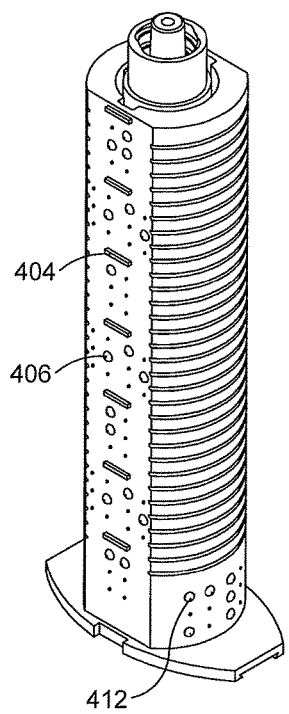
FIG. 22 shows one face of the barrel having raised indicia representing major graduations and major unit numbers.

Referring to FIGS. 21-29, a fourth embodiment of a syringe including a dosage indicator for aiding the visually impaired is shown generally at reference numeral 400. Syringe 400 is similar to syringe 100 and 200, and therefore like parts are labeled with like reference numbers. Syringe 400 differs in terms of the dosage indicator arrangement and raised indicia. Specifically, syringe 400 includes a barrel 402 of generally cylindrical cross-section having diametrically opposed flat faces carrying raised indicia presented for use by the user. As best shown in FIG. 22, one side of the barrel 402 may be marked with raised indicia corresponding to major graduations 404 and major unit numbers 406. The major graduations may be marked using raised lines indicating larger increments corresponding to the volume in the syringe reservoir, for example. Major unit numbers corresponding to the major graduation markings may be provided in Braille adjacent their respective graduation.

Figure 23:
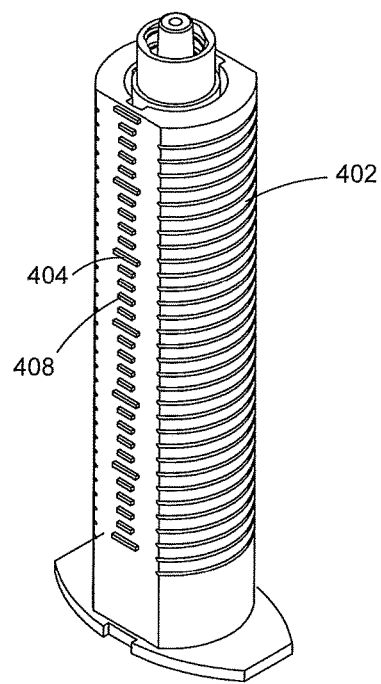
FIG. 23 shows the opposing face of the barrel having raised indicia representing major and minor graduations.
Figure 24:
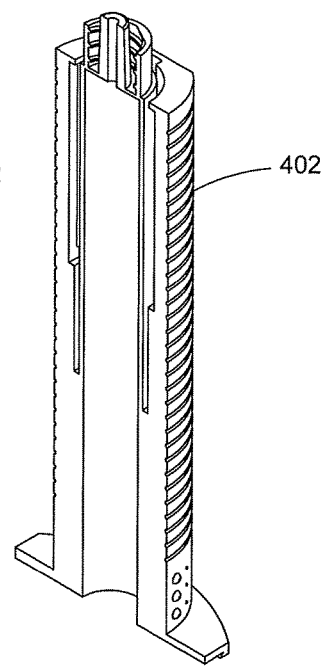
FIG. 24 is a sectional view through the barrel.

As best shown in FIG. 23, the opposing face of the barrel 402 may be marked with raised indicia including both major graduations 404 and minor graduations 408. Major graduations 404 may be represented using relatively long lines, and the minor graduations 408 therebetween may be represented using relatively short lines in comparison. The types of markings, groupings, and graduations may be customized, for example, based on the type of medication, common dosages, user, etc. FIG. 24 shows the barrel 402 in cross-section.

Figure 25:
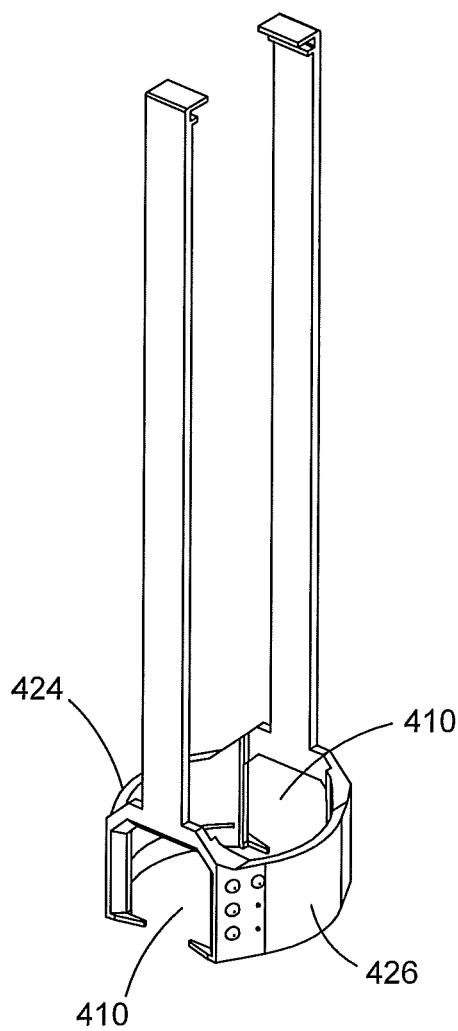
FIG. 25 is an isometric view of an embodiment of a dosage indicator having a dosage window.
Figure 26:
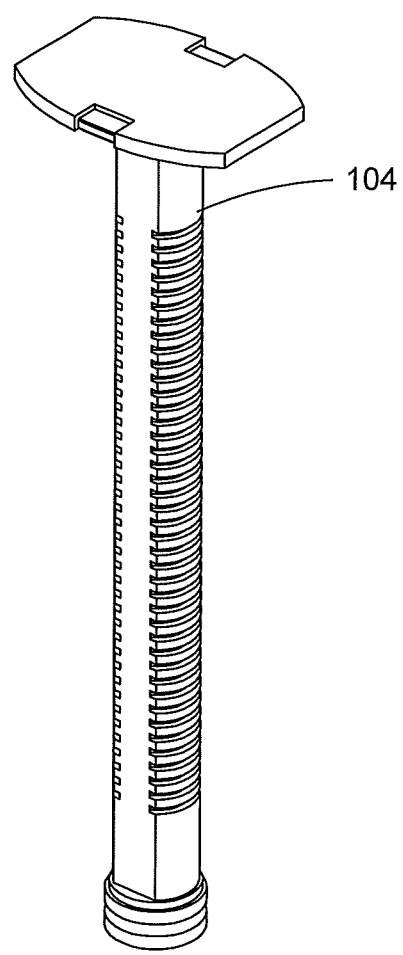
FIG. 26 is an isometric view of an embodiment of a plunger having detents for controlling axial movement of the plunger relative to a barrel.

Referring to FIG. 25, the dosage indicator 424 includes a collar 426 configured to slide along the longitudinal length of the barrel 402 as the plunger 104 moves relative to the barrel. The collar 426 includes diametrically-opposed windows 410 that align over the underlying indicia (e.g., major graduated markings, minor graduated markings, major unit numbers, units, etc.) on the opposing flat faces of the barrel 402. The barrel indicia are visible and prominently displayed through the windows 410 of the collar 426 such that the visually impaired user is able to determine the dosage. By utilizing raised indicia, the user is able to feel the raised indicia displayed in the window(s) in order to determine the position of the dosage indictor 424 along the length of the barrel 402, and consequently the current volume of medication in the syringe reservoir. For example, a window may be sized to simultaneously present both the major graduated marking and the corresponding Braille unit in the same window. One or more of the barrel 402 and the dosage indicator 424 may be marked with unit indicia (e.g., Braille) to indicate the unit of measure of each part, to ensure that the right dosage indicator is used with the right barrel.

Figures 27A, 27B, 27C, 27D:
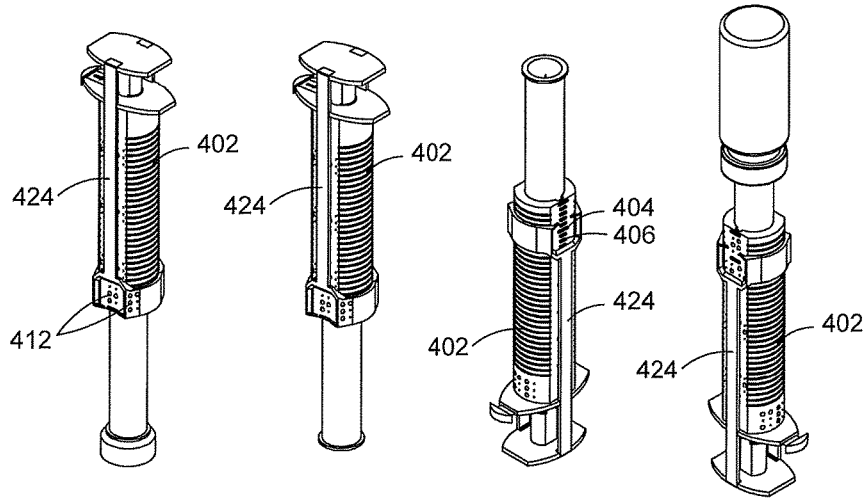
FIGS. 27a-27i are sequential views illustrating the preparation, loading, readying and use of the syringe of FIG. 21.
Figures 27E, 27F, 27G, 27H, 27I:
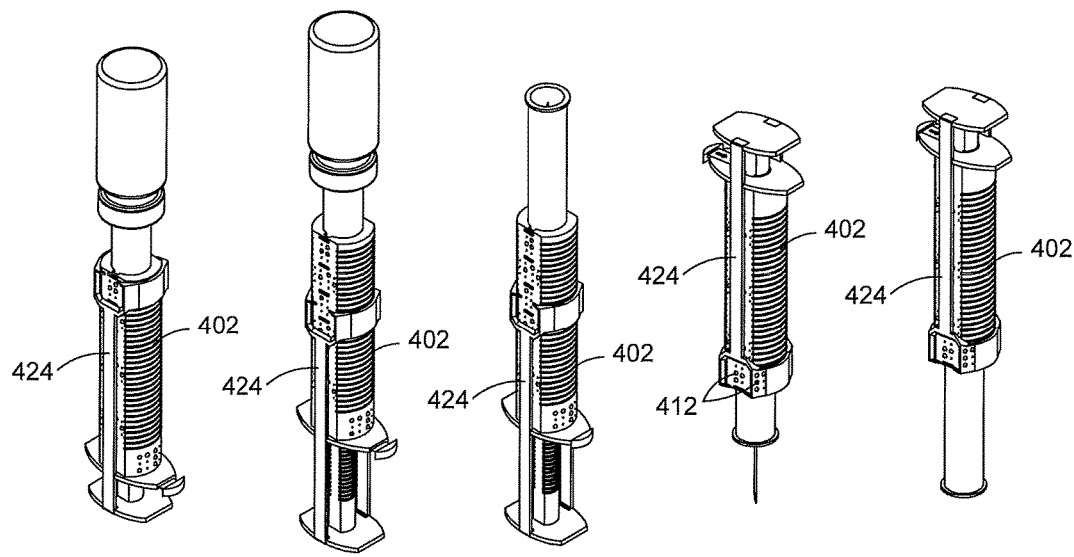

FIGS. 27a-i are sequential views illustrating the preparation, loading and use of a syringe according to the fourth embodiment of the invention. It should be understood that these sequential steps may be applied to any of the syringe embodiments disclosed herein. Referring to FIG. 27a, a syringe is provided with the plunger retracted into the barrel 402, the dosage indicator 424 set to zero indicated at Braille marking 412, the needle guard fully extended, and a removable/disposable safety cap attached to the needle guard. Referring to FIG. 27b, the removable/disposable cap is removed before use. Referring to FIG. 27c, the lock is moved to the non-operative position or "unlocked" to allow the plunger to be withdrawn from the barrel 402. Referring to FIG. 27d, the needle is advanced into a medication ampoule as the needle guard simultaneously retracts. Referring to FIG. 27e, the plunger is pushed to the zero position to remove any air. Referring to FIG. 27f, the plunger is withdrawn to the predetermined dosage amount indicated through the window of the dosage indicator 424. Referring to FIG. 27g, the lock is moved to the operative position or "locked" into engagement with the plunger to prevent the plunger from unintentionally moving axially relative to the barrel 402, and the vial is removed. Referring to FIG. 27h, using the needle guard as a guide to align the injection area, the lock is disengaged, the needle is inserted into the patient, and the plunger depressed to deliver the dosage. Finally, referring to FIG. 27i, the lock may be engaged and the safety cap replaced before discarding the syringe.

Figure 28:
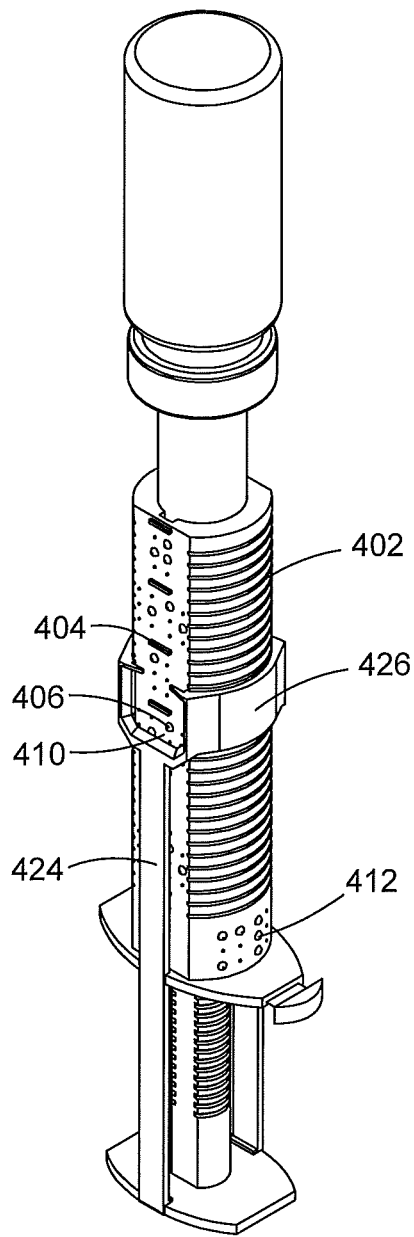
FIG. 28 shows the syringe being loaded with the major graduations and major unit numbers visible through one face of the dosage indicator.
Figure 29:
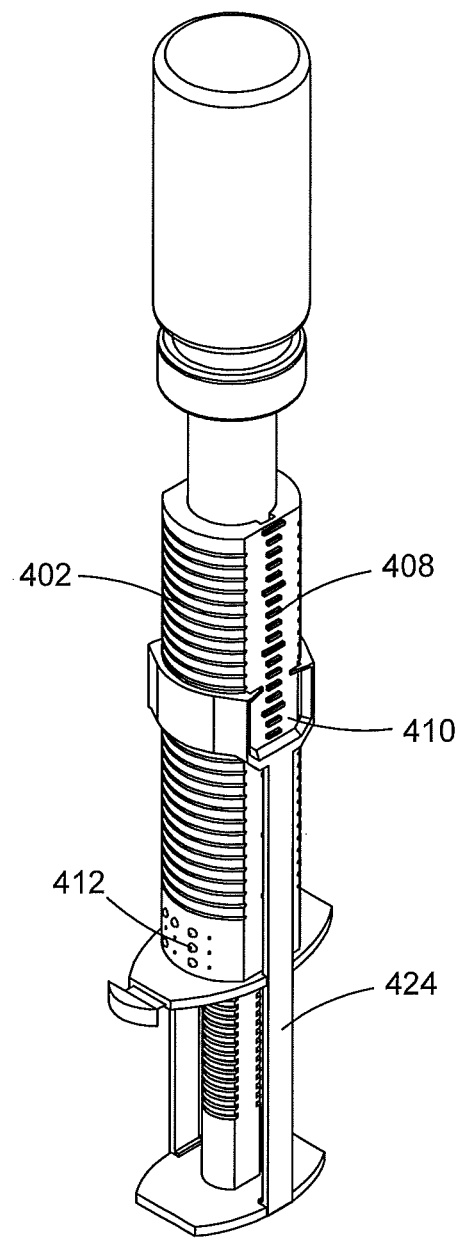
FIG. 29 shows the opposing face of the dosage indicator displaying the major and minor graduations therethrough.

FIG. 28 shows syringe 400 having withdrawn a predetermined dosage from a medication ampoule. The plunger is withdrawn from the barrel 402 a predetermined amount to load a predetermined dosage. The medication type, maximum dosage, etc. may be indicated at Braille markings 412. The dosage indicator 424 is moved axially along the longitudinal length of the barrel 402 such that the collar 426 is positioned with respect to the barrel to display the correct/predetermined dosage through the dosage window 410. The major graduations 404 and raised Braille 406 are visible through the window and able to be felt by the user to determine the dosage in the syringe. FIG. 29 shows the opposing face of the barrel and dosage indicator displaying the major and minor graduations 410, 408 through the opposing dosage indicator window.

Figure 30:
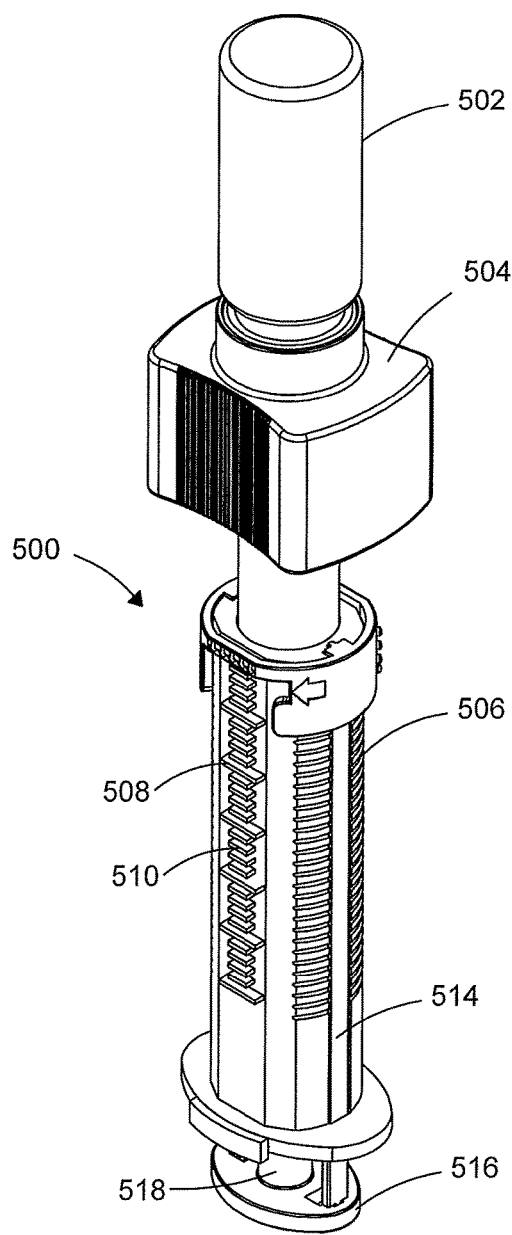
FIG. 30 is an isometric view of a syringe according to a fifth embodiment of the invention.
Figure 31:
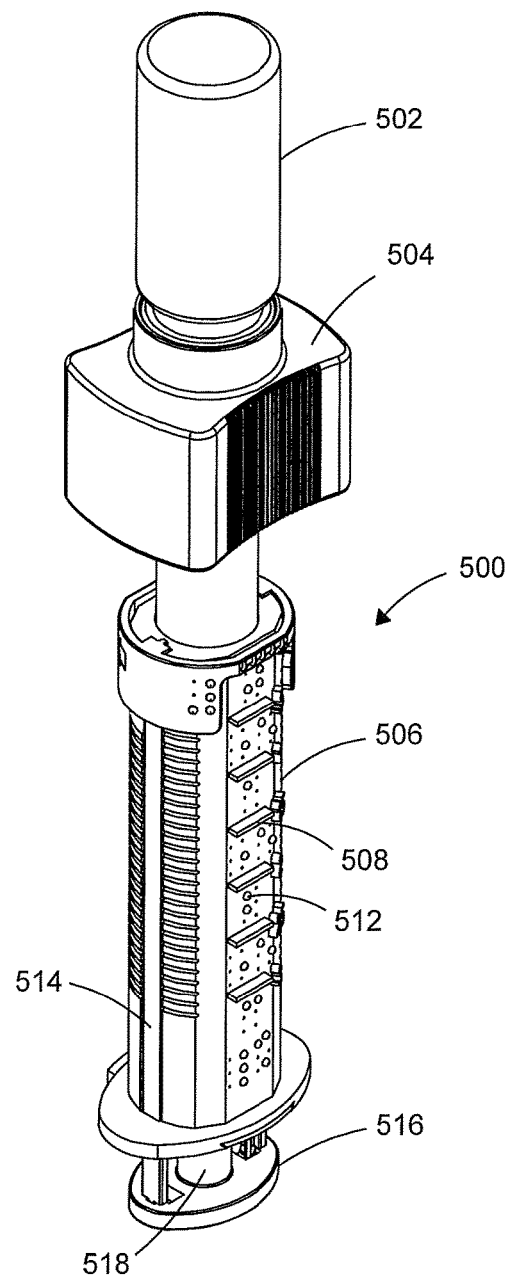
FIG. 31 is another isometric view of the syringe of FIG. 30 and including an ampoule guide.
Figure 32:
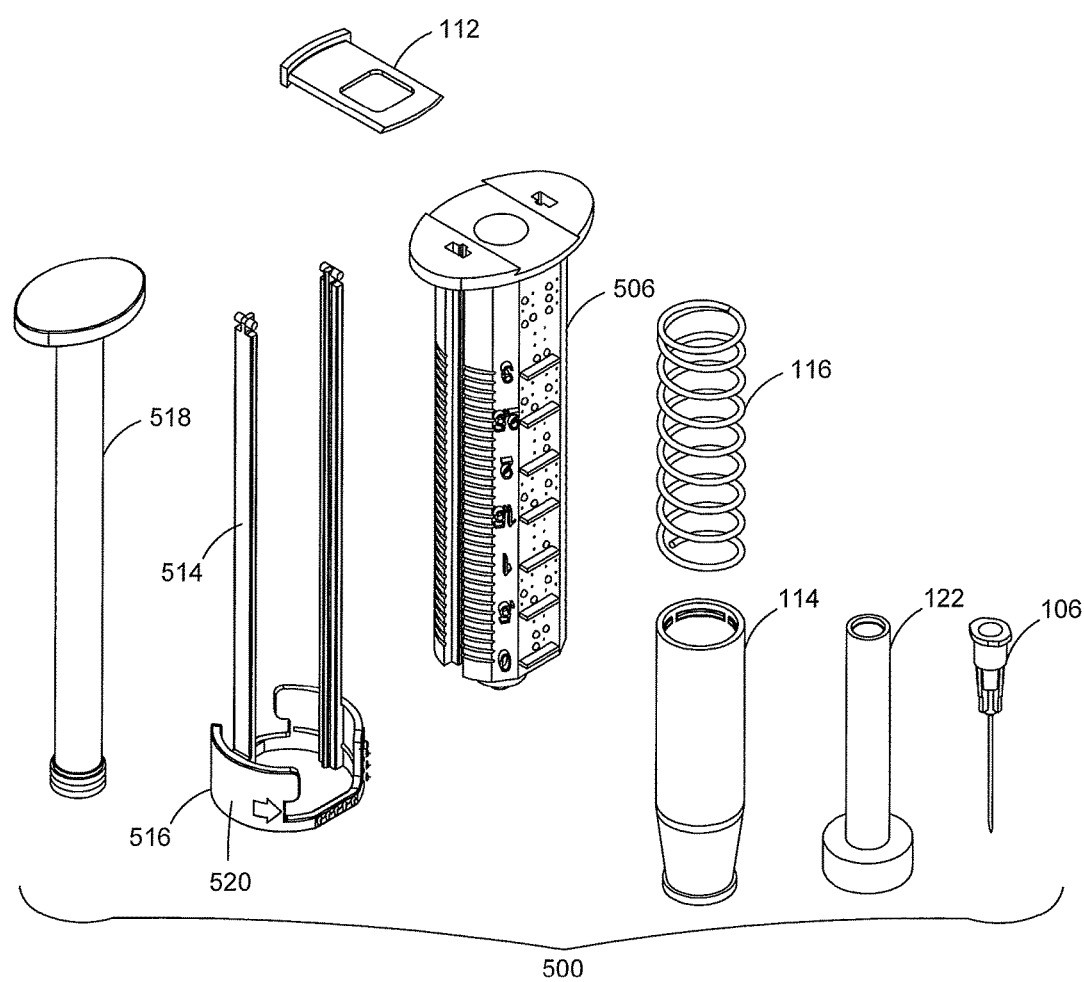
FIG. 32 shows the parts of the syringe of FIG. 30.
Figures 33, 34:
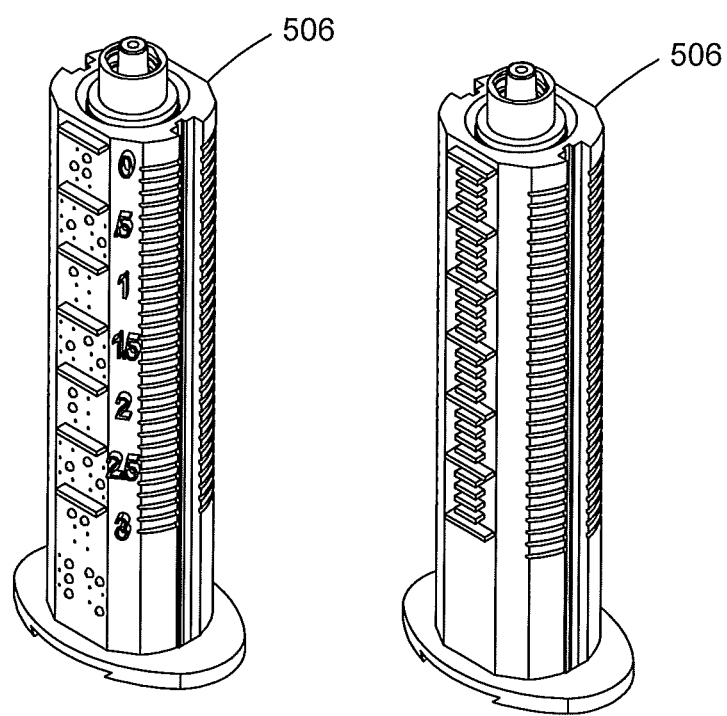
FIG. 33 shows one face of the barrel having raised indicia representing major graduations and major unit numbers.
FIG. 34 shows the opposing face of the barrel having raised indicia representing major and minor graduations.
Figures 35, 36:
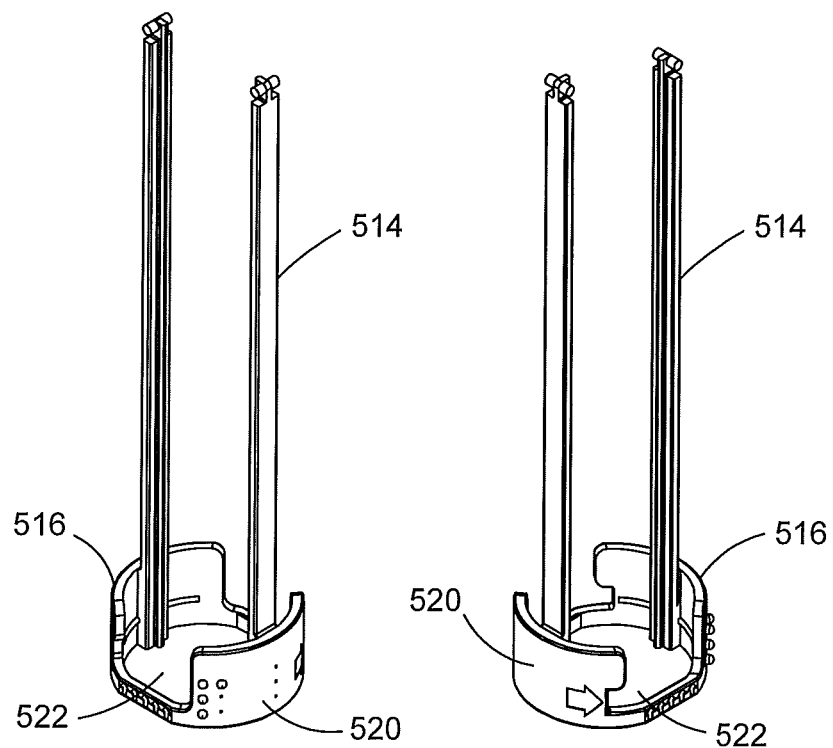
FIG. 35 is an isometric view of the dosage indicator shown in FIG. 30.
FIG. 36 is another isometric view of the dosage indicator shown in FIG. 30.

Referring to FIGS. 30-36, a fifth embodiment of a syringe including a dosage indicator for aiding the visually impaired is shown generally at reference numeral 500. Referring specifically to FIGS. 30 and 31, syringe 500 is shown positioned to withdraw medication from an ampoule 502. An intermediate guide 504 is used to align the needle guard of the syringe with the ampoule 502 to aid in alignment and prevent accidental needle sticks. One flat face of the barrel 506 carries major and minor graduations 508, 510, while the opposing flat face of the barrel carries major graduations 508 and Braille markings 512.

As compared to the syringe embodiments discussed above, the parallel arms 514 of the dosage indicator 516 are guided by and travel within recessed guides longitudinally arranged along the length of the barrel 506. As such, the parallel arms 514 sit flush with the barrel to resist snagging and protect them from damage, among other advantages.

The barrel 506 includes the features discussed above including a medication reservoir, indicia, finger flange, luer lock, channel for receiving the plunger lock, chamber for the needle guard and guide, channels for the dosage collar aims, and the features on the outer surface to produce vibration and sound. The plunger 518 includes the features discussed above including grooves in the stem for achieving alignment with the major and minor graduated markings, and prevent movement when the plunger lock is engaged.

The collar 520 includes the opposing dosage windows 522 that indicate to the user the current volume of medication in the medication reservoir. As shown, the dosage windows are generally rectangular in shape to prominently display the graduations and/or Braille. The windows 522 may be sized to display only a single Braille number or unit and major graduation so that there can be no confusion as to the indicated dosage. The minor graduations 510 may function to finely tune the dosage indicated in the dosage windows 522. uzed to are sized so that only a single by way of alignment with the graduated markings. Like in the above embodiments, the collar 520 and plunger are interconnected through the parallel arms 514.

Figure 37:
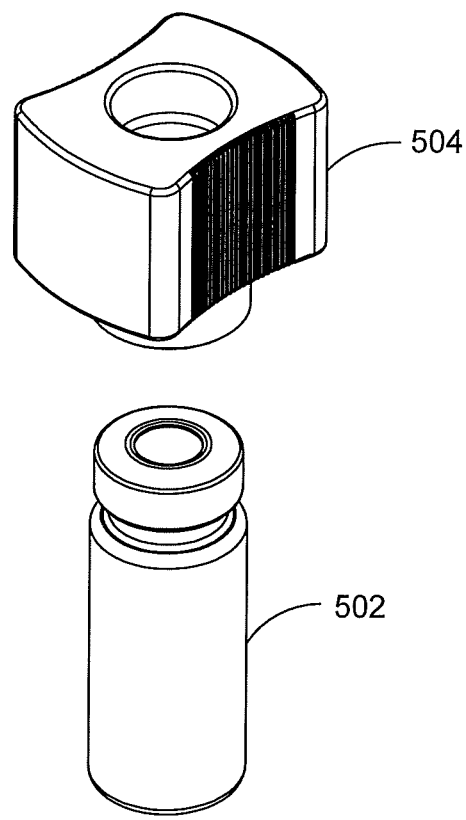
FIG. 37 shows an ampoule guide for ensuring proper alignment of a syringe and medication ampoule.

Referring to FIG. 37, the guide 504 is a separate piece used to align the ampoule 502 and syringe to facilitate alignment and withdrawal from the ampoule. The guide 504 defines an axial passageway therethrough shaped at one end to interface with or receive the cap or top of the ampoule, and shaped at the opposing end to interface with or receive the retractable needle guard of the syringe. The outer surface of the guide 504 may be shaped to facilitate gripping.

While the dosage indicator configurations have been described herein with reference to a hypodermic-type syringe having a needle, it is envisioned that the dosage indicator configurations may be adapted to and implemented with other syringe types and injection devices.

The foregoing description provides embodiments of the invention by way of example only. It is envisioned that other embodiments may perform similar functions and/or achieve similar results. Any and all such equivalent embodiments and examples are within the scope of this disclosure.

What is claimed is:

1. A syringe, comprising:
a barrel having an internal reservoir for containing a volume of medication;
a plunger received within the barrel and axially movable relative thereto to change the volume of the medication in the internal reservoir; and
a dosage indicator movable with the plunger, the dosage indicator in contact with the barrel such that at least one of an audible alert and a tactile alert is produced upon movement of the dosage indicator relative to the barrel, the dosage indicator comprising a collar positioned around the barrel configured to slide along a length of the barrel as the plunger moves axially, an interior of the collar contacting external features on the barrel to produce the at least one of an audible alert and a tactile alert to indicate collar movement, and the collar attached to a plunger flange of the plunger through a pair of parallel spaced arms arranged to travel along an outer surface of the barrel within elongate slots recessed into the outer surface of the barrel.

2. The syringe of claim 1, wherein the parallel spaced arms travel along diametrically opposing flat faces of the barrel.

3. The syringe of claim 1, wherein the collar includes an internal feature that contacts the external features on the barrel to provide stepped motion of the collar along the length of the barrel.

4. The syringe of claim 1, wherein the collar includes a window aligned with a face of the barrel such that dosage indicia marked on the barrel is displayed through the window.

5. The syringe of claim 1, wherein the collar includes a pair of diametrically opposing windows aligned with respective diametrically opposing flat faces of the barrel, and wherein raised dosage indicia marked on the opposing flat faces of the barrel is displayed through the windows.

6. The syringe of claim 1, wherein the barrel is marked with raised indicia including at least one of braille, numbers, major graduations and minor graduations.

7. The syringe of claim 1, further comprising a needle guard configured to retract into the barrel to expose a needle attached to one end of the barrel.

8. The syringe of claim 7, wherein the needle guard is biased in a direction away from the plunger.

9. The syringe of claim 1, further comprising a lock arranged on a barrel flange of the barrel movable into and out of contact with the plunger, the lock movable between a first position preventing relative axial movement between the barrel and the plunger and a second position allowing relative axial movement between the barrel and the plunger.

10. The syringe of claim 1, wherein the barrel includes diametrically opposing flat faces, wherein one flat face is marked with raised indicia including braille and major graduations and the opposing flat face is marked with raised indicia including major and minor graduations.

11. The syringe of claim 1, wherein the plunger includes external features that contact internal features on the collar positioned atop a barrel flange of the barrel.

12. A syringe configured to produce at least one of an audible and a tactile alert to a visually impaired user to indicate dosage of a medication, comprising:
   a barrel having an internal reservoir for containing a volume of the medication;
   a plunger received within the barrel and axially movable relative thereto to change the volume of the medication in the internal reservoir; and
   a dosage indicator movable with the plunger, the dosage indicator including a collar positioned around the barrel configured to produce at least one of an audible and a tactile alert in response to relative movement between the plunger and the barrel, the collar configured to slide along a length of the barrel as the plunger moves axially to produce the at least one of an audible alert and a tactile alert to indicate collar movement, and the collar attached to a plunger flange of the plunger through a pair of parallel spaced arms arranged to travel along an outer surface of the barrel within elongate slots recessed into the outer surface of the barrel.

13. The syringe of claim 12, wherein the collar includes a window aligned with a flat face of the barrel such that raised dosage indicia marked on the barrel is presented through the window.

14. The syringe of claim 12, wherein the collar includes a pair of diametrically opposing windows aligned with respective diametrically opposing flat faces of the barrel, and wherein raised dosage indicia marked on the opposing flat faces of the barrel is presented through the windows.

15. The syringe of claim 12, wherein the barrel is marked with raised indicia including at least one of braille, numbers, major graduations and minor graduations.

16. The syringe of claim 12, further comprising a needle guard configured to retract into the barrel to expose a needle attached to one end of the barrel, wherein the needle guard is biased in a direction away from the plunger.

* * * * *